(12) United States Patent
Sato et al.

(10) Patent No.: US 7,520,970 B2
(45) Date of Patent: Apr. 21, 2009

(54) IMMOBILIZATION SUPPORT, PROCESS FOR PRODUCING THE SAME, ELECTRODE, PROCESS FOR PRODUCING THE SAME, ELECTRODE REACTION UTILIZING APPARATUS AND PROCESS FOR PRODUCING THE SAME

(75) Inventors: Atsushi Sato, Kanagawa (JP); Tokuji Ikeda, Kyoto (JP); Kenji Kano, Kyoto (JP)

(73) Assignee: Sony Corporation, Tokyo (JP)

( * ) Notice: Subject to any disclaimer, the term of this patent is extended or adjusted under 35 U.S.C. 154(b) by 274 days.

(21) Appl. No.: 10/555,368

(22) PCT Filed: May 21, 2004

(86) PCT No.: PCT/JP2004/007335

§ 371 (c)(1), (2), (4) Date: Nov. 2, 2005

(87) PCT Pub. No.: WO2004/108918

PCT Pub. Date: Dec. 16, 2004

(65) Prior Publication Data

US 2006/0105418 A1 May 18, 2006

(30) Foreign Application Priority Data

Jun. 5, 2003 (JP) ............................. 2003-161272
Sep. 5, 2003 (JP) ............................. 2003-313462

(51) Int. Cl.
*C12M 1/00* (2006.01)
*C25B 11/06* (2006.01)
*C12Q 1/68* (2006.01)
*C12N 11/08* (2006.01)
*C12N 1/00* (2006.01)

(52) U.S. Cl. .............................. 204/403.1; 204/403.11; 204/403.14; 205/777.5; 429/43; 429/249; 435/6; 435/25; 435/29; 435/180; 435/181; 435/289.1; 435/817

(58) Field of Classification Search ........................ None
See application file for complete search history.

(56) References Cited

U.S. PATENT DOCUMENTS 5,407,818 A * 4/1995 von Gentzkow et al. .... 435/180
6,051,389 A * 4/2000 Ahl et al. ....................... 435/10
6,338,790 B1 * 1/2002 Feldman et al. ........... 205/777.5
6,461,496 B1 * 10/2002 Feldman et al. ........... 205/777.5
6,551,494 B1 * 4/2003 Heller et al. .............. 205/777.5
2002/0179457 A1 * 12/2002 Heller ......................... 205/775

FOREIGN PATENT DOCUMENTS

| DE | 293 597 A5 | 9/1991 |
| JP | 3-28081 A | 12/1991 |
| JP | 8-196274 A | 8/1996 |
| JP | 8-296177 A | 11/1996 |
| WO | WO 03/025627 | 3/2003 |
| WO | WO 03/025627 A2 | 3/2003 |

OTHER PUBLICATIONS

Suye S. et al., "Immobilization of glucose oxidase on poly-(L-lysine)-modified polycarbonate membrane", Biotechnol.Appl. Biochem. 1998, 27(3), pp. 245-248, GB.

Mizutani, F. et al., "Rapid measurement of transaminase activities using an amperometric L-glutamate-sensing electrode based on a glutamate oxidase-polyion complex-bilayer membrane.", Sensors and Actuators B-Chemical, 1998, 52(1-2), pp. 23-29.

Sato A. et al., "Thermal stability and electron transfer reaction of modified myoglobin immobilized on a carbon electrode in poly(ethylene oxide) oligomers." Electrochimica Acta, 2001, 46(10-11), pp. 1729-1735, AU.

Sato A. et al., "Diaphorase/napthoquinone derivative-modified electrode as an anode for diffusion-controlled oxidation of NADH in electrochemical cells.", Chemistry Letters, Oct. 2003, 32(10), pp. 880-881, JP.

Mizutani F et al.; "Rapid measurement of transaminase activities using an amperometric L-glutamate-sensing electrode based on a glutamate oxidase-polyion complex-bilayer membrane"; Sep. 15, 1998; Sensors and Actuators B, Elsevier Sequoia S.A., Lausanne, CH; pp. 23-29; XP004152944; Issn: 0925-4005.

Suye S. et al., "Immobilization of glucose oxidase on poly-(L-lysine)-modified polycarbonate membrane", Biotechnol. Appl. Biochem. vol. 27, No. 3, 1998, pp. 245-248, XP002980867.

* cited by examiner

*Primary Examiner*—Herbet J. Lilling
(74) *Attorney, Agent, or Firm*—Robert J. Depke; Rockey, Depke & Lyons, LLC.

(57) ABSTRACT

An immobilization carrier containing an electron acceptor compound is used in addition to glutaraldehyde and poly-L-lysine to immobilize an enzyme and an electron acceptor compound simultaneously to an electrode. For example, here are used diaphorase as the enzyme and 2-amino-3-carboxy-1,4-naphthoquinone (ACNQ) as the electron acceptor compound.

2 Claims, 9 Drawing Sheets

IMMOBILIZATION SUPPORT, PROCESS FOR PRODUCING THE SAME, ELECTRODE, PROCESS FOR PRODUCING THE SAME, ELECTRODE REACTION UTILIZING APPARATUS AND PROCESS FOR PRODUCING THE SAME

This application is a 371 U.S. National Stage filing of PCT/JP2004/007335, filed May 21, 2004, which claims priority to Japanese Patent Application Number 2003-161272, filed Jun. 5, 2003, and Japanese Patent Application Number 2003-313462 filed Sep. 5, 2003, all of which are incorporated herein by reference.

TECHNICAL FIELD

The present invention relates to an immobilization carrier, its manufacturing method, electrode, its manufacturing method, electrode reaction-utilizing device and its manufacturing method that are suitable for application to various kinds of electrode reaction-utilizing devices following biological metabolism and using it as electrode reaction, such as biosensors, bioreactors, bio-fuel cells, and so forth.

BACKGROUND ART

Biological metabolism in living beings is a reaction mechanism with high matrix selectivity and remarkably high efficiency. It is characterized in reaction progressing in a relatively moderate atmosphere held at the room temperature and neutral. Biological metabolism herein pertains involves aspiration and photosynthesis, among others, which converts oxygen and various kinds of nutritional elements such as sugars, fats, oils, and proteins to energy necessary for growth of microorganisms and cells.

Such biological reactions largely rely on biological catalysts made of proteins, namely, enzymes. The idea of using the catalytic reaction of enzymes has been put into practice from early days of the history of humankind. Its applications range over many industrial fields including brewing industry, fermentation industry, fiber industry, leather industry, food industry and drug industry. Recently, its applications to the field of electronics such as biosensors, bioreactors, bio-fuel cells, which incorporate the catalytic function into electrode systems, have come to be examined and brought into practice.

Enzymes are composed of proteins, and usually instable to heat, strong acids, strong alkalis, organic solvents, and the like. Therefore, enzymes could be used only in water solutions. To bring about enzymatic reaction, the batch process has been used heretofore, which dissolves an enzyme into a water solution to have it act on the matrix. However, there is an extreme technical difficulty in recovery and re-use of enzymes out of the solution after reaction without degeneration of the enzymes. Thus, the method results in disposing of enzymes after each reaction, and this must be an uneconomical way of use.

Under the background, there is a proposal of water-insoluble immobilization enzymes. Once being insolubilized to water, highly specific enzymes can be handled in the same manner as solid catalysts used in ordinary chemical reactions. This is a very useful way of use of enzymes.

Much the same is true on application of enzymes to electrode systems. High-density immobilization of an enzyme on an electrode makes it possible to efficiently catch enzymatic reactions occurring near the electrode as electric signals. For researches of electrode systems, in general, it is necessary to use an electron acceptor compound behaving as an electron transfer medium between the protein as the enzyme and the electrode, where intermediation of electrons is unlikely to occur. Preferably, this electron acceptor compound is immobilized similarly to the enzyme.

Methods of immobilizing enzymes are roughly classified to two groups, i.e. entrapping methods and the binding methods. Entrapping methods are further classified to lattice-type one and microcapsule type one. On the other hand, binding methods are further classified to the absorption method, covalent binding method (cross-linking method), and others, depending upon the binding mode.

The entrapping method envelops the enzyme with a water-insoluble, semi-permeable polymer not binding to the enzyme itself. A merit of this method is that the possibility of damaging the enzymatic activity is low because the immobilization takes place under a relatively mild condition. On the other hand, since the enzyme are not eluted upon immobilization while the reaction matrix of the enzyme must have voids easy to pass, it is necessary to select an appropriate entrapping agent every time when the combination of the enzyme and the matrix varies.

The absorption method uses ionic absorption or physical absorption of enzymes. Although this method employs easy ways of immobilization, the state of absorption is susceptible to service conditions, and absorption and desorption of enzymes tend to become instable. Therefore, this method cannot be a general technique for immobilization.

The covalent binding method uses amino groups, carboxyl groups of enzymes for binding by the use of a cross-linking agent. Although this method can stably immobilize enzymes relatively easily, it often invites inactivation of the enzyme because the cross-linking agent may modify a portion near the active center of the enzyme or the conditions for cross-linking may be severe for the enzyme.

A manufacturing method of a functional electrode has been proposed, which impregnates a porous electrode with a monomer for generating a conductive polymer and a supporting electrolyte, and brings about electrolytic oxidization in the support electrolyte solution to make a conductive polymer coat on the entire surface inside the porous electrode (Japanese Patent Laid-open Publication No. JP-H06-271655). In addition, a method of measuring optical isomers such as D-lactic acid, L-lactic acid, and so on, has been proposed (Japanese Patent Laid-open Publication No. JP-H06-121697).

As reviewed above, those conventional immobilization methods have respective demerits, and an effort is required to determine an immobilization method optimum for each enzyme-matrix combination. Furthermore, upon determining immobilization to electrode systems, since immobilization of the electron acceptor compound as the electron transport medium is also desirable as mentioned above, here is required immobilization capable of retaining respective abilities of the enzyme, electron acceptor compound and matrix, which makes determination of an immobilization method more difficult.

It is therefore an object of the invention to provide an immobilization carrier suitable for realizing a highly efficient functional electrode incorporating catalytic function of an enzyme by immobilizing the enzyme to an electrode system or immobilizing the enzyme and an electron acceptor compound simultaneously, an electrode function-utilizing device and their manufacturing methods.

DISCLOSURE OF INVENTION

As a result of vigorous studies to overcome the above problems, the Inventors found it effective to use an immobilization carrier using glutaraldehyde and poly-L-lysine as the cross-linking agents. It is effective to combine an electron acceptor compound, especially having amino groups, preferably in addition to these cross-linking agents. Further studies lead to the result that it is effective to use as the cross-linking agent an immobilization carrier containing a first compound (such as glutaraldehyde mentioned above) having two or more groups capable of polymerizing with a compound having amino groups or imino groups and a second compound (such as poly-L-lysine mentioned above) having amino groups or imino groups, of an immobilization carrier containing a third compound having two or more groups capable of polymerizing with a compound having carboxyl groups and a fourth compound having carboxyl groups.

The present invention has been made based on those studies.

That is, to solve those problems, the first aspect of the present invention is an immobilization carrier comprising glutaraldehyde and poly-L-lysine.

The second aspect of the present invention is an immobilization carrier comprising a structure in which glutaraldehyde and poly-L-lysine are coupled by cross-linking.

Glutaraldehyde (glutar-dialdehyde) includes two aldehyde groups to form Schiff bases, and has been used as a cross-linking reagent. However, actual enzyme immobilization using glutaraldehyde alone is limited in the amount of enzyme immobilization, and incomplete in ex-membrane elution of the enzyme. On the other hand, L-lysine forming poly-L-lysine (polypeptide) is a kind of α-amino acid and it exists as constituent amino acid of almost all proteins. Since it has primary amino groups at lateral chains, it has abundant positive electric charge and no toxicity. Because of its abundant positive electric charge, poly-L-lysine is sometimes used as the immobilization carrier in the poly-ion complex method that is a quasi-electrostatic function with an enzyme having negative electric charge. However, it is subject to the ambient electric charge balance, and largely varies in enzyme immobilization amount and stability with the service condition. In addition, there are only few practical examples of simultaneous immobilization of enzyme/electron acceptor compound using these immobilization schemes and materials, and there have been no report of a highly efficient functional electrode concurrently ensuring an acceptable amount of enzyme/electron acceptor compound and retention of activities and free from rate controlling of the entire reaction by the enzyme immobilization electrode.

In contrast, in the first and second aspects of the invention, by using the immobilization carrier composed of glutaraldehyde and poly-L-lysine as mentioned above, the respective enzyme immobilizing performance can be improved greatly, and excellent enzyme immobilizing performance can be obtained as the entirety of the immobilization carrier.

Composition ratio of glutaraldehyde and poly-L lysine may be arbitrarily determined in general, although its optimum value varies with the immobilizing enzyme and the associated matrix.

In the first and second aspects of the invention, the immobilization carrier preferably contains an electron acceptor compound. Basically, the electron acceptor compound may be any compound provided it can exchange electrons with the electrode relatively easily when the immobilization carrier is formed in an electrode. Preferably, however, the electron acceptor compound additionally contains amino groups. When the electron acceptor compound is combined with a cross-linking agent composed of glutaraldehyde and poly-L-lysine, it can function to support the cross-linking between glutaraldehyde and poly-L-lysine.

The immobilization carrier may contain a compound other than the electron acceptor compound, if necessary.

The third aspect of the present invention is an immobilization carrier comprising a first compound having at least two groups capable of polymerizing with a compound having amino groups or imino groups, and a second compound having amino groups or imino groups.

The fourth aspect of the present invention is an immobilization carrier comprising a structure in which a first compound having at least two groups capable of polymerizing with a compound having amino groups or imino groups and a second compound having amino groups or imino groups are coupled by cross-linking.

The fifth aspect of the present invention is an immobilization carrier comprising a third compound having at least two groups capable of polymerizing with a compound having carboxyl groups and a fourth compound having carboxyl groups.

The sixth aspect of the present invention is an immobilization carrier comprising a structure in which a third compound having at least two groups capable of polymerizing with a compound having carboxyl groups and a fourth compound having carboxyl groups are coupled by cross-linking.

The seventh aspect of the present invention is an electrode comprising an immobilization carrier containing glutaraldehyde and poly-L-lysine, and an enzyme.

The eighth aspect of the present invention is an electrode comprising an immobilization carrier that contains a first compound having at least two groups capable of polymerizing with amino groups or imino groups, and a second compound containing amino groups or imino groups; and an enzyme.

The ninth aspect of the present invention is an electrode comprising an immobilization carrier having a structure in which a first compound having at least two groups capable of polymerizing with amino groups or imino groups and a second compound containing amino groups or imino groups are coupled by cross-linking; and an enzyme.

The tenth aspect of the present invention is an electrode comprising an immobilization carrier containing a third compound having at least two groups capable of polymerizing with a compound having carboxyl groups, and a fourth compound having carboxyl groups; and an enzyme.

The eleventh aspect of the present invention is an electrode comprising an immobilization carrier containing a third compound having at least two groups capable of polymerizing with a compound having carboxyl groups, and a fourth compound having carboxyl groups; and an enzyme.

The twelfth aspect of the present invention is an electrode reaction-utilizing device using an electrode containing an immobilization carrier and an enzyme, characterized in that the immobilization carrier comprises a first compound having at least two groups capable of polymerizing with a compound having amino groups or imino groups, and a second compound having amino groups or imino groups.

The thirteenth aspect of the present invention is an electrode reaction-utilizing device using an electrode containing an immobilization carrier and an enzyme, characterized in that the immobilization carrier has a structure in which a first compound having at least two groups capable of polymerizing with a compound having amino groups or imino groups and a second compound having amino groups or imino groups are coupled by cross-linking.

The fourteenth aspect of the present invention is an electrode reaction-utilizing device using an electrode containing an immobilization carrier and an enzyme, characterized in that the immobilization carrier contains a third compound having at least two groups capable of polymerizing with a compound having carboxyl groups and a fourth compound having carboxyl groups.

The fifteenth aspect of the present invention is an electrode reaction-utilizing device using an electrode containing an immobilization carrier and an enzyme, characterized in that the immobilization carrier has a structure in which a third compound having at least two groups capable of polymerizing with a compound having carboxyl groups and a fourth compound having carboxyl groups are coupled by cross-linking.

The sixteenth aspect of the present invention is a method of manufacturing an immobilization carrier, comprising: polymerizing a first compound having at least two groups capable of polymerizing with a compound having amino groups or imino groups and a second compound having amino groups or imino groups.

The seventeenth aspect of the present invention is a method of manufacturing an immobilization carrier, comprising: polymerizing a third compound having at least two groups capable of polymerizing with a compound having amino groups or imino groups and a fourth compound having amino groups or imino groups.

The eighteenth aspect of the present invention is a method of manufacturing an electrode, comprising: immobilizing an enzyme to an immobilization carrier containing a first compound having at least two groups capable of polymerizing with amino groups or imino groups and a second compound having amino groups or imino groups.

The nineteenth aspect of the present invention is a method of manufacturing an electrode, comprising: immobilizing an enzyme to an immobilization carrier containing a third compound having at least two groups capable of polymerizing with a compound having carboxyl groups and a fourth compound having carboxyl groups.

The twentieth aspect of the present invention is a method of manufacturing an electrode, comprising: immobilizing an enzyme to an immobilization carrier obtained by polymerization of a first compound having at least two groups capable of polymerizing with a compound having amino groups or imino groups and a second compound having amino groups or imino groups.

The twenty-first aspect of the present invention is a method of manufacturing an electrode, comprising: immobilizing an enzyme to an immobilization carrier obtained by polymerization of a third compound having at least two groups capable of polymerizing with a compound having carboxyl groups and a fourth compound having carboxyl groups.

The twenty-second aspect of the present invention is a method of manufacturing an electrode reaction-utilizing device using an electrode containing an immobilization carrier and an enzyme, comprising the step of:

manufacturing the electrode by immobilizing the enzyme to the immobilization carrier containing a first compound having at least two groups capable of polymerizing with a compound having amino groups or imino groups and a second compound having amino groups or imino groups.

The twenty-third aspect of the present invention is a method of manufacturing an electrode reaction-utilizing device using an electrode containing an immobilization carrier and an enzyme, comprising the step of:

manufacturing the electrode by immobilizing the enzyme to the immobilization carrier containing a third compound having at least two groups capable of polymerizing with a compound having carboxyl groups with a fourth compound having carboxyl groups.

The twenty-fourth aspect of the present invention is a method of manufacturing an electrode reaction-utilizing device using an electrode containing an immobilization carrier and an enzyme, comprising the step of:

manufacturing the electrode by immobilizing the enzyme to the immobilization carrier obtained by polymerization of a first compound having at least two groups capable of polymerizing with a compound having amino groups or imino groups and a second compound having amino groups or imino groups.

The twenty-fifth aspect of the present invention is a method of manufacturing an electrode reaction-utilizing device using an electrode containing an immobilization carrier and an enzyme, comprising the step of:

manufacturing the electrode by immobilizing the enzyme to the immobilization carrier obtained by polymerization of a third compound having at least two groups capable of polymerizing with a compound having carboxyl groups and a fourth compound having carboxyl groups.

In the third to twenty-fifth aspects of the present invention, composition ratio between the first compound and the second compound, and composition ratio between the third compound and the fourth compound, may be arbitrarily determined in general, although their optimum values vary with the compounds used, immobilizing enzymes and associated matrixes. These aspects of the invention are common to the first and second aspects of the invention in that the immobilization carrier is preferred to additionally contain an electron acceptor compound and may contain a compound other than the electron acceptor compound, if necessary.

Examples of the first to fourth compounds used as the cross-linking agent (cross-linking reagent) are shown below. In the following examples of the cross-linking agent, R or R' represents at least one compound selected from the group consisting of aliphatic hydrocarbons, cycloaliphatic hydrocarbons, aromatic hydrocarbons, cyclodextrins including $\alpha$, $\beta$, $\gamma$-cyclodextrins, crownether, calixarenes, peptides, enzymes, coloring dyes, and so on. R and R' may be either different or identical.

As compounds that can cross-link with $NH_2$ groups of the enzyme, or $NH_2$ of the electron acceptor agent if the immobilization carrier contains the electron acceptor compound having $NH_2$, one or more compounds selected from the following examples of cross-liking agents can be used. Glutaraldehyde is a kind of aldehyde (R—CHO).

Carboxylic acid (R—COOH)
Peracid (R—CO(OOH))
Thiocarboxylic acid (R—CSOH)
Isocyanides (R—NC)
Cyanic acid esters (R—OCN)
Isocyanic acid esters (R—NOC)
Thiocyanic acid esters (R—SCN)
Aldehyde (R—CHO)
Thioaldehyde (R—CHS)
Ketone (R—CO—R')
Thioketone (R—CS—R')
Thiol (R—SH)
Imine (R=NH)
Peroxides (R—OOR')

As compounds that can cross-link with COOH groups of the enzyme, or COOH groups of the electron acceptor compound if the immobilization carrier contains the electron acceptor compound having COOH groups, one or more compounds selected from the following examples of cross-linking agents can be used.

Amine (R—NH$_2$, RR'NH)
Peroxides (R—CO(OOH))
Thiocarboxylic acid (R—CSOH)
Ester (R—COOR')
Halides (R—X, X: halogen atoms)
Acid halides (R—COX, X: halogen atoms)
Amide (R—CONH$_2$)
Hydrazide (R—CO—NHNH$_2$)
Imide (R—CO—NH—OC—R')
Amidine (R—CNH(NH$_2$))
Nitrile (R—CN)
Imine (R=NH) (such as polyethylene imine)
Dendrimers (such as polyamide amine and polypropylene imine) are also usable.

The enzyme immobilizing method according to the invention is applicable to any enzymes, preferably having amino groups as functional groups of the enzyme protein, although it is not indispensable. A single kind of enzyme may be used, or two or more kinds of enzymes may be used in combination. It is also acceptable to use one or more kinds of enzymes requiring a coenzyme and one or more kinds of enzymes requiring no coenzyme in combination. Examples of enzymes include diaphorase known as an oxidation-reduction enzyme of NADH (reduced nicotinamide adenine dinucleotide)/NAD$^+$(nicotinamide adenine dinucleotide), glucose dehydrogenase (NAD-dependent enzyme), and so on.

Here is explained classification of enzymes (IUBMB: International Union of Biochemistry and Molecular Biology/ Enzyme Nomenclature Committee).

Enzymes are classified by enzyme codes (EC numbers), and roughly classified to the following six classes (EC1-EC6).

EC1; Oxidoreductase (Oxidation-Reduction Enzymes)

All of enzymes related to oxidation and reduction are classified in this class. They occupy about 26% of the enzyme table.
[Examples] alcohol dehydrogenase (EC1.1.1.1]
diaphorase (EC1.6.99.-] (diaphorase used in an embodiment of the invention explained later is also classified here.)

Subsequently, they are sub-classified by second and third numerals. Fourth numerals are numbers given after authorization by the committee.

In the above examples,
[EC1.1. - - - ]: enzymes acting upon CH—OH of donors (among oxidation-reduction enzymes)
[EC1.6. - - - ]: enzymes acting upon NADH or NADPH EC2; Transferase (Transfer Enzymes)

They catalyze reactions for transferring certain functional groups of a compound (donor) to another compound (acceptor).
[Examples] aspartate carbamoyltransferase
[EC2.1.3.2]
hexokinase [EC2.7.1.1]

EC3; Hydrolase (Hydrolytic Enzymes)
They catalyze hydrolysis of the matrix.
[Examples] β-amylase [EC3.2.1.2]
pepsin A [EC3.4.23.1]

EC4; Lyase
Here belong enzymes that catalyze reactions retaining double bond by elimination reaction from C—C bond, C—O bond, C—N bond, and so forth, and the opposite reactions.
[Example] oxaloacetate decarboxylase [EC4.1.1.3]
fumarate hydratase [EC4.2.1.2]

EC5; Isomerase (Isomerizing Enzymes)
They catalyze isomerizing reactions.
[Example] alanine racemase [EC5.1.1.1]
triose-phosphate isomerase [EC5.3.1.1]

EC6; Ligase (Synthetic Enzymes)
They catalyze synthetic reactions.
[Example] tyrosine-tRNA ligase [EC6.1.1.1]
acetate-CoA ligase [EC6.2.1.1]

To ensure the function of enzyme, a low-molecular organic compound called coenzyme is sometimes required in addition to the enzyme and the matrix, which compound couples the enzyme and does an operation indispensable for the reaction. Preferably, the coenzyme is immobilized like the enzyme and the electron acceptor compound. NADH and NAD$^+$, as well as NADPH (reduced nicotinamide adenine dinucleotide phosphoric acid) and NADP (nicotinamide adenine dinucleotide phosphoric acid) are examples of these coenzymes.

Material of the electrode may be any substance provided it is conductive and insoluble to water. Such substances may be used either singly or in combination with other substances. In the case where a material having a large surface area, such as carbon felt or activated carbon is used as the material of the electrode, it is expected to increase the immobilized quantity of the enzyme and the electron acceptor compound per unit volume.

Examples of the electrode reaction-utilizing device are biosensors, bioreactors and bio fuel cells among others.

According to the invention having the above-summarized construction, since the first compound and the second compound contained in the immobilization carrier couple by cross-linking, or the third compound and the fourth compound couple by cross-linking, that is, glutaraldehyde and poly-L-lysine couple by cross-linking, it is possible to make polymers that can take sufficiently long and substantially free three-dimensional structures. Then, by using the immobilization carrier for immobilizing an enzyme to an electrode, the enzyme can be entrapped by the polymer in a favorable form. Further, by using the electron acceptor compound contained in the immobilization carrier, electron transfer between the enzyme and the electrode can be facilitated.

BEST MODE FOR CARRYING OUT THE INVENTION

An embodiment of the invention is explained below with reference to the drawings.

This embodiment uses an immobilization carrier containing an electron acceptor compound in addition to glutaraldehyde and poly-L-lysine to simultaneously immobilize the enzyme and the electron acceptor compound, or the enzyme, coenzyme and electron acceptor compound, to an electrode. The electron acceptor compound may include or may not include amino groups.

Figure 1:
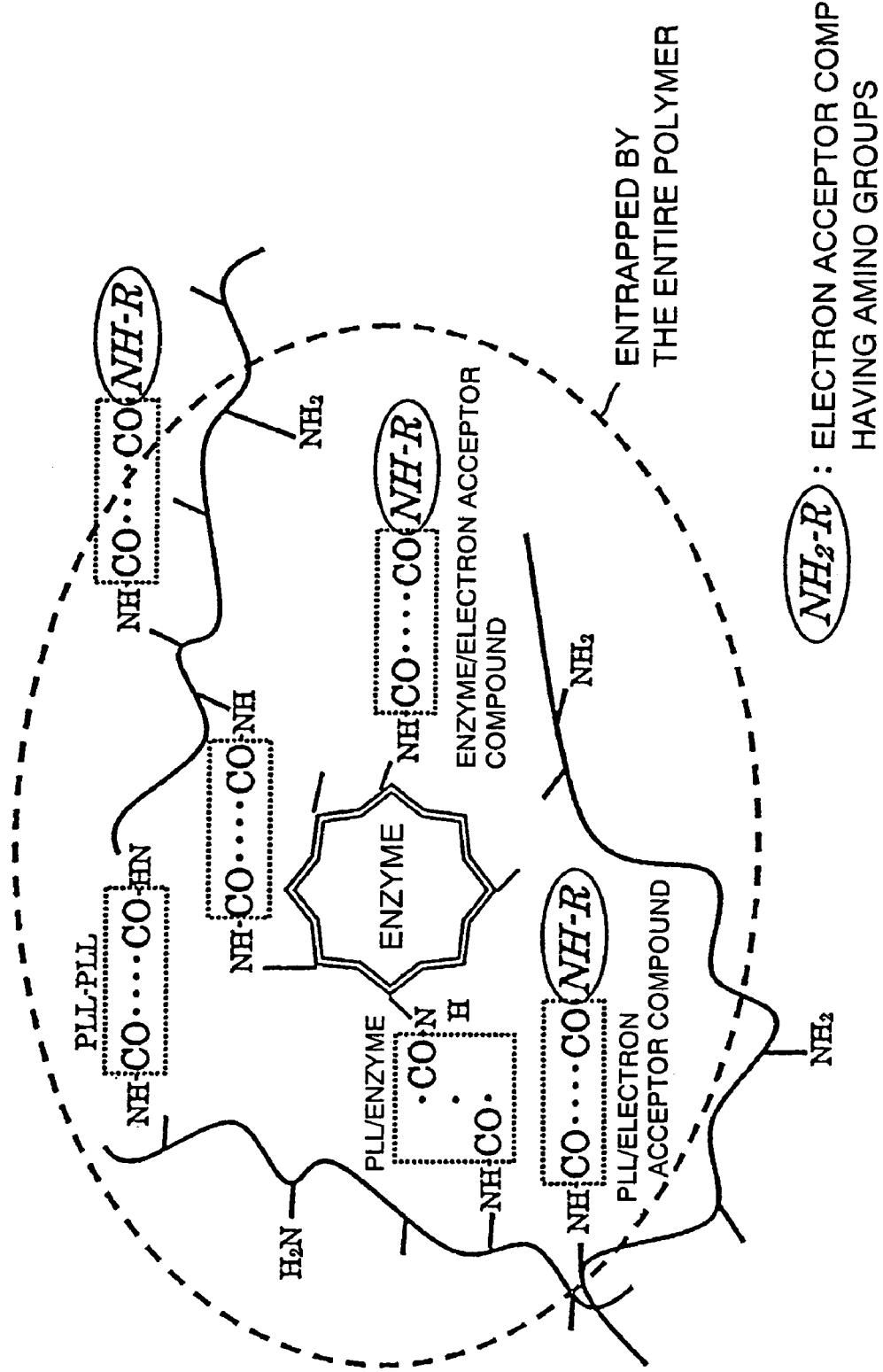
FIG. 1 is a schematic diagram showing an image of simultaneous immobilization of an enzyme and an electron acceptor compound on an electrode by an immobilization carrier in an embodiment of the invention.

An image of simultaneous immobilization of an enzyme and an electron acceptor compound on an electrode by an immobilization carrier is shown in FIG. 1. Assume that the immobilization carrier contains the electron acceptor compound having amino groups in addition to glutaraldehyde and poly-L-lysine and the enzyme has amino groups. In FIG. 1, PLL represents poly-L-lysine, and $NH_2$—R represents the electron acceptor compound having amino groups. As shown in FIG. 1, two aldehyde groups at opposite ends of glutaraldehyde cross-link the amino groups of poly-L-lysine to form an amide linkage, and thereby form a polymer that is sufficiently long and can take a substantially free three-dimensional structure. The entirety of this polymer entraps the enzyme having amino groups (the oval broken line shows an image of entrapping). In addition, since the enzyme and the electron acceptor compound have amino groups here as well, the aldehyde group at one end of glutaraldehyde and the amino group of poly-L-lysine can form an amide linkage, and the aldehyde group at the other end of glutaraldehyde and the amino group of the enzyme can simultaneously form an amide linkage to cross-link. Alternatively, the aldehyde group at one end of glutaraldehyde and the amino group of poly-L-lysine can form an amide linkage, and the aldehyde group at the other end of glutaraldehyde and the amino group of the electron acceptor compound can simultaneously form an amide linkage to cross-link. Alternatively, the aldehyde group at one end of glutaraldehyde and the amino group of the enzyme can form an amide linkage and the aldehyde group at the other end of glutaraldehyde and the amino group of the electron acceptor compound can simultaneously form an amide linkage to cross-link. The structure shown in FIG. 1 is an example of poly-ion complex.

Next explained are some examples.

EXAMPLE 1

Figure 2:
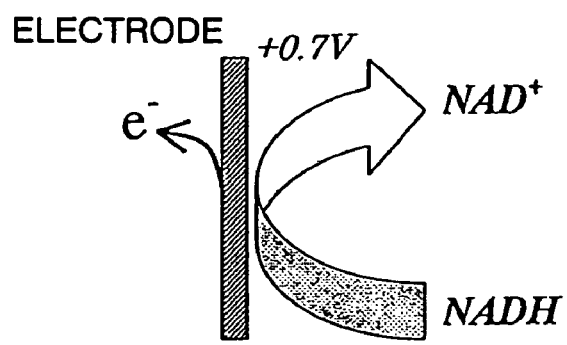
FIG. 2 is a schematic diagram showing a reaction mechanism model in the case where NADH is oxidized electrochemically.
Figure 3:
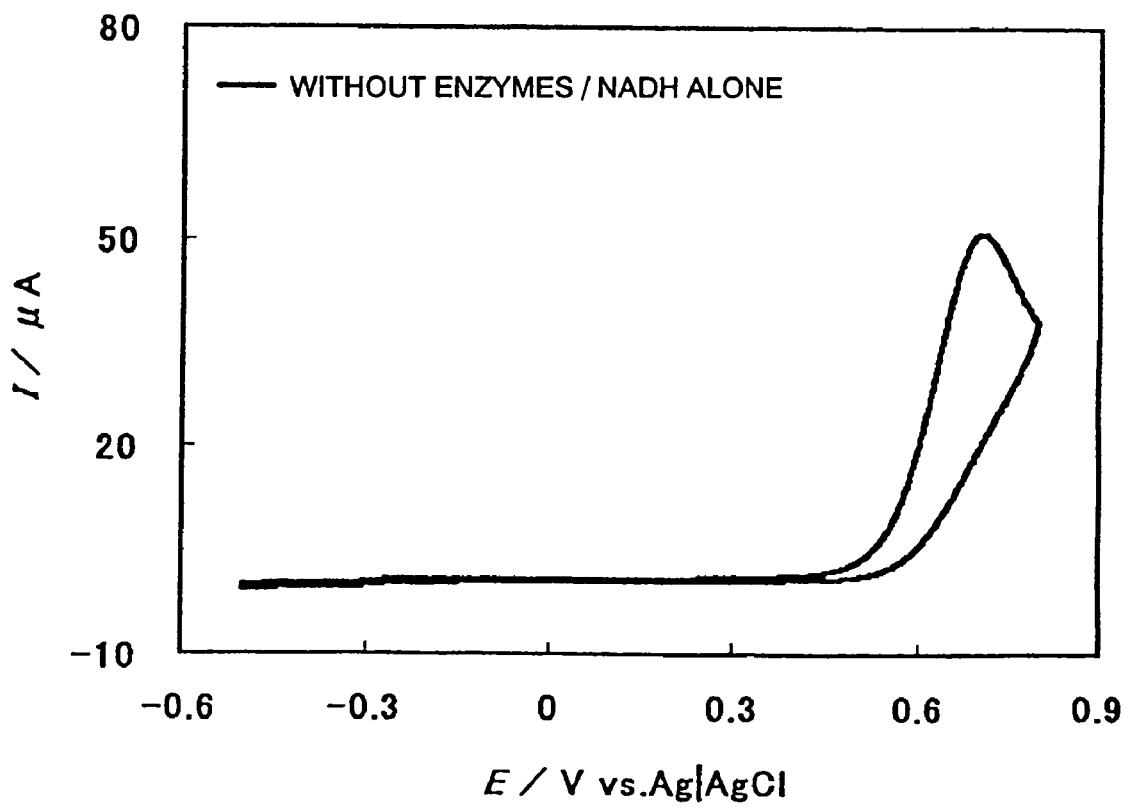
FIG. 3 is a schematic diagram showing a cyclic voltamogram of direct oxidation wave in the case where NADH is oxidized electrochemically.
Figure 4:
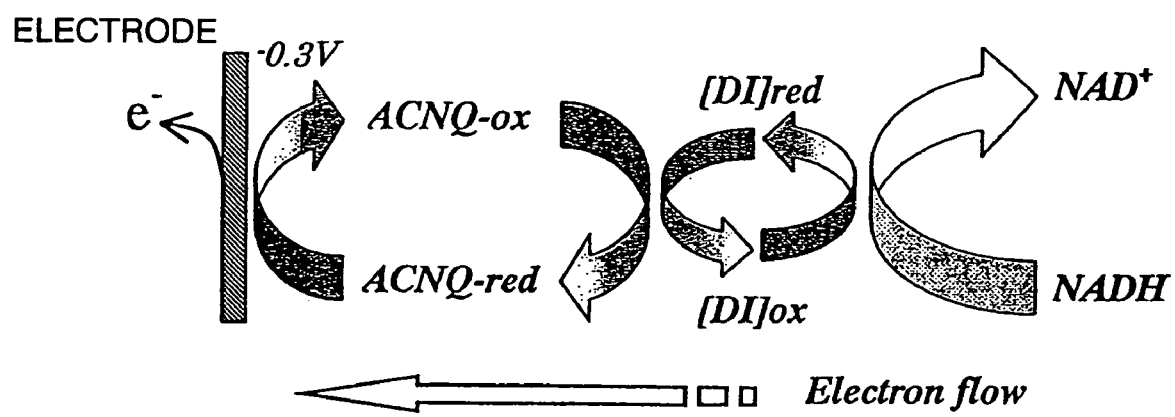
FIG. 4 is a schematic diagram showing a reaction mechanism model in the case where NADH is oxidized electrochemically by using diaphorase and ACNQ.

First evaluated is NADH oxidazability of a functional electrode on which diaphorase as an enzyme and 2-amino-3-carboxy-1,4-naphthoquinone (ACNQ) as an electron acceptor compound having amino groups are immobilized. In the case of a reaction system not using diaphorase, NADH is directly oxidized on the electrode to $NAD^+$ and releases electrons ($e^-$) as shown in FIG. 2. Thus, it appears as a peak near 0.7 V on a cyclic voltamogram (CV) as shown in FIG. 3. As such, a large overvoltage is required for direct oxidization of NADH on the electrode. Therefore, the enzyme-immobilized electrode must have the function of efficiently reducing the overvoltage and efficiently oxidizing NADH. FIG. 4 shows a NADH oxidization mechanism via diaphorase (DI) and ACNQ. NADH is oxidized via diaphorase-ACNQ. On CV, its condition is observed as a catalytic current near −0.3 V that is the oxidation-reduction potential of ACNQ, and oxidization overvoltage of NADH is reduced. Experimental conditions are shown below.

Figure 5A:
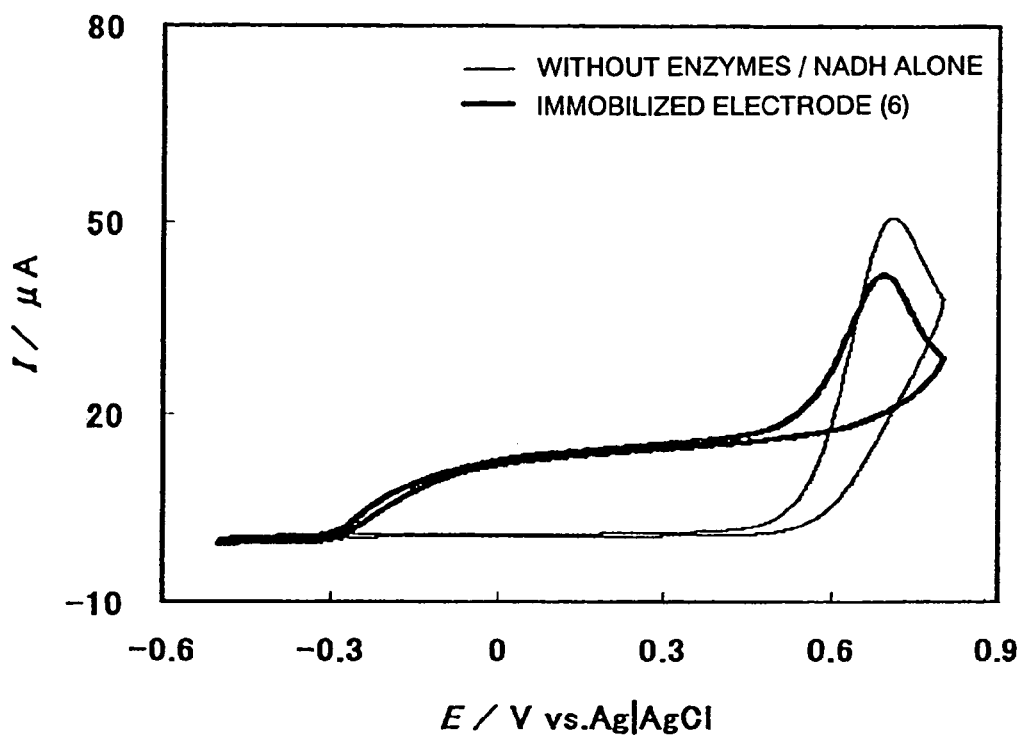
FIG. 5A and FIG. 5B are schematic diagrams showing sigmoid-type and peak-type cyclic voltamograms in catalytic current.
Figure 5B:
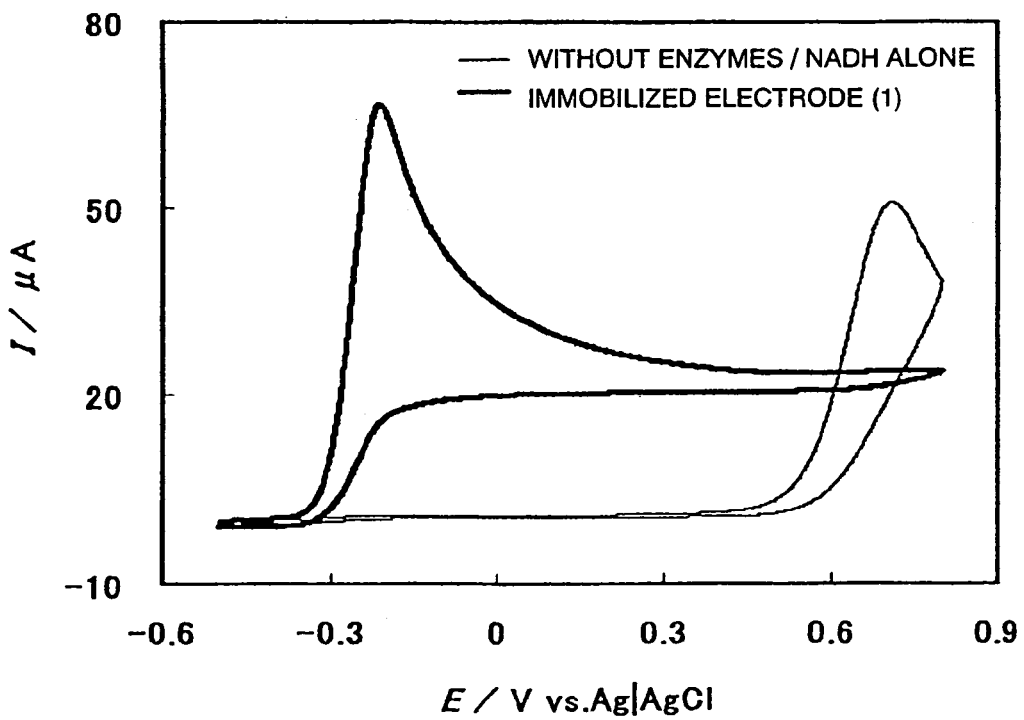

An electrolysis cell made of polytetrafluoroethylene and having the capacity of 1 ml was used as a reaction vessel, and electrochemical oxidation reaction of NADH was conducted by applying a voltage. 1 ml of phosphoric acid buffer solution of pH 8.0 was poured into the reaction vessel as an aqueous buffer solution, and after 15 minutes of nitrogen gas substitution, a sufficient amount of NADH phosphoric acid buffer solution (10 mM) was added. Platinum wire as the counter electrode was immersed into the reaction vessel, and a silver (Ag)/silver chloride (AgCl) electrode was used as the reference electrode. After that, 2 μl of phosphoric acid buffer solution (47 μM) of diaphorase (Unitika, from *Bacillus stearothermophilus*), 2.8 μl of ACNQ ethanol solution (10 mM), 3 μl of glutaraldehyde water solution (0.125%) and 3 μl of poly-L-lysine water solution (1%) were poured on a glassy carbon electrode (BAS, φ=3.0 mm), and blended well. Then, after being air-dried at the room temperature, the electrode was rinsed with distilled water, and completed as a diaphorase/ACNQ immobilized electrode. For comparison purposes, immobilized electrodes were prepared by changing the composition ratio of seeping quantities of glutaraldehyde and poly-L-lysine to the combination of 2 μl and 4 μl and the combination of 4 μl and 2 μl within the same total amount 6 μl, while maintaining the same seeping quantities of diaphorase and ACNQ (2 μl and 2.8 μl), and other immobilized electrodes were prepared by using 6 μl of glutaraldehyde alone and 6 μl of poly-L-lysine alone, individually, in the same manner. Then, diaphorase/ACNQ immobilized portion was immersed into phosphoric acid buffer solution. These counter electrodes, reference electrodes and diaphorase/ACNQ-immobilized electrodes were connected to a potentiostat, and reactions were observed electrochemically by potential sweeping by potential scanning method (cyclic voltannmetry, CV). The swept potential range was −0.5-01V and maximum catalytic current values observed in this range are shown in Table 1. The enzymes, reagents, devices and experimental atmospheres used for the experiment were constant throughout the tests, relative merits in terms of quantities of immobilization of enzyme-immobilized portions, stability, film properties, and so on, appear in form of differences of maximum catalytic current values. Corresponding shapes of curves on CV are shown as well in the table. Samples by combination of glutaraldehyde and poly-L-lysine can be confirmed advantageous in comparison with samples each using the same amount of only one of them, respectively ((1) and (2) vs. (4) and (5) in Table 1). About shapes of curves on CV, FIG. 5A (sigmoid type ((6) in Table 1)) and FIG. 5B (peak type ((1) in Table 1)) show respective examples. Sigmoid type catalytic current is a current suggesting the limit of electrode performance (electrode performance rate control), and direct oxidation wave appearing near 0.7 V demonstrates that NADH remains sufficiently. In contrast, peak type catalytic current observed in samples by combination of glutaraldehyde and poly-L-lysine demonstrates the supply rate control of NADH as the matrix.

Because no direct oxidation wave of NADH is observed near 0.7 V, it suggests that NADH near the electrode was entirely consumed for enzyme reaction, and such electrodes can be appreciated as high-function electrodes available for further increase of current values.

TABLE 1

| | Conditions for immobilization | | | | |
|---|---|---|---|---|---|
| | Cross-linking reagent | Amount added (μl) | Enzyme/ electron transmitting medium | Max. catalytic current value (μl) | CV shapes |
| (1) | GA + PLL | 3 + 3 | DI, ACNQ | 67.5 | Peak |
| (2) | GA + PLL | 2 + 4 | DI, ACNQ | 58.9 | Peak |
| (3) | GA + PLL | 4 + 2 | DI, ACNQ | 10.7 | Sigmoid |
| (4) | GA | 6 | DI, ACNQ | 24.9 | Sigmoid |
| (5) | PLL | 6 | DI, ACNQ | 7.49 | Sigmoid |
| (6) | GA + PLL | 3 + 3 | DI | 13.1 | Sigmoid |
| (7) | Dissolved | — | DI, ACNQ | 0.663 | Sigmoid |
| (8) | GA + PLL | 3 + 3 | DI, VK3 | 26.4 | Sigmoid |
| (9) | GA | 6 | DI, VK3 | 18.1 | Sigmoid |
| (10) | PLL | 6 | DI, VK3 | 6.82 | Sigmoid |

Abbreviations in the Table
GA: glutaraldehyde;
PLL: poly-L-Lysine;
DI: diaphorase

EXAMPLE 2

The same experiment was conducted by using measuring devices similar to those used for Example 1 and changing the conditions of enzyme-immobilized electrodes. There were prepared diaphorase-immobilized electrodes by pouring 2 μl of diaphorase alone and immobilizing it while maintaining the same seeping amounts (3 μl each) of glutaraldehyde and poly-L-lysine as compared with the fabricating method of the immobilized electrodes according to Example 1. Maximum catalytic current values there obtained are shown in Table 1. Neither diaphorase nor ACNQ is immobilized on electrodes. As compared with samples dissolved in a phosphoric acid solution (non-fixed conditions), it is demonstrated that diaphorase-immobilized electrodes are advantageous in terms of catalytic current obtained ((6) vs. (7) in Table 1) and combination of glutaraldehyde and poly-L-lysine enables immobilization of the enzyme alone. However, as compared with the results of Example 1, it is appreciated that simultaneous immobilization of ACNQ having amino groups is more desirable for electrode performance ((1) vs. (6) in Table 1).

EXAMPLE 3

Figure 6A:
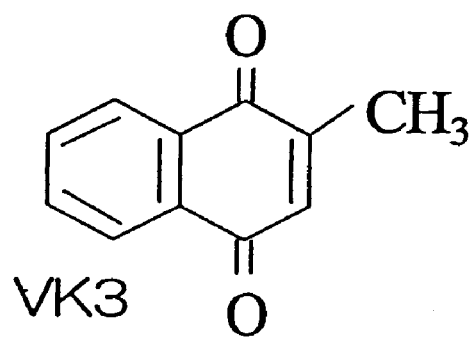
FIG. 6A and FIG. 6B are schematic diagrams showing structures of VK3 and ACNQ.
Figure 6B:
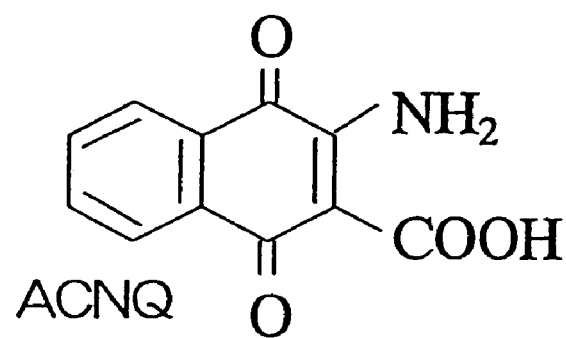

Samples were prepared by using 2-methyl-3-carboxy-1,4-naphthoquinone (vitamin K3, VK3) and combining glutaraldehyde and poly-L-lysine (3 μl each) as compared with the method of fabricating immobilized electrodes according to Example 1, and in addition, VK3-immobilized electrodes using 6 μl of one of glutaraldehyde and poly-L-lysine, respectively. Then, similar measurement of those samples was conducted under the same conditions. Concentration of the poured VK3 was determined to make the same amount as the case of ACNQ. FIG. 6A shows a structure of VK3. Except that amino groups do not exist, the structure of FIG. 6A is similar to the structure of ACNQ shown in FIG. 6B, and their electrochemical properties tend to exhibit similar tendencies. Maximum catalytic current values then obtained are shown n Table 1. Combination of glutaraldehyde and poly-L-lysine was suggested to be more advantageous than the use of respective one of them also in VK3 having no amino groups ((8 vs. (9) and (10) in Table 1). However, Results of Example 1 also demonstrate that the use of ACNQ as the electron acceptor compound is more advantageous and that simultaneous immobilization of an electron acceptor compound having amino groups is more advantageous for electrode performance ((1) vs. (8) in Table 1). Also when glucose oxidase is used as the enzyme, similar tendencies have been confirmed.

It is appreciated from Examples 1 to 3 that immobilization carriers composed of glutaraldehyde and poly-L-lysine is useful and applicable to any enzymes and any electron acceptor compounds. However, immobilization carriers having amino groups are advantageous for use to electron acceptor compounds in terms of electrode performance and stability of immobilized sites.

EXAMPLE 4

Figure 7:
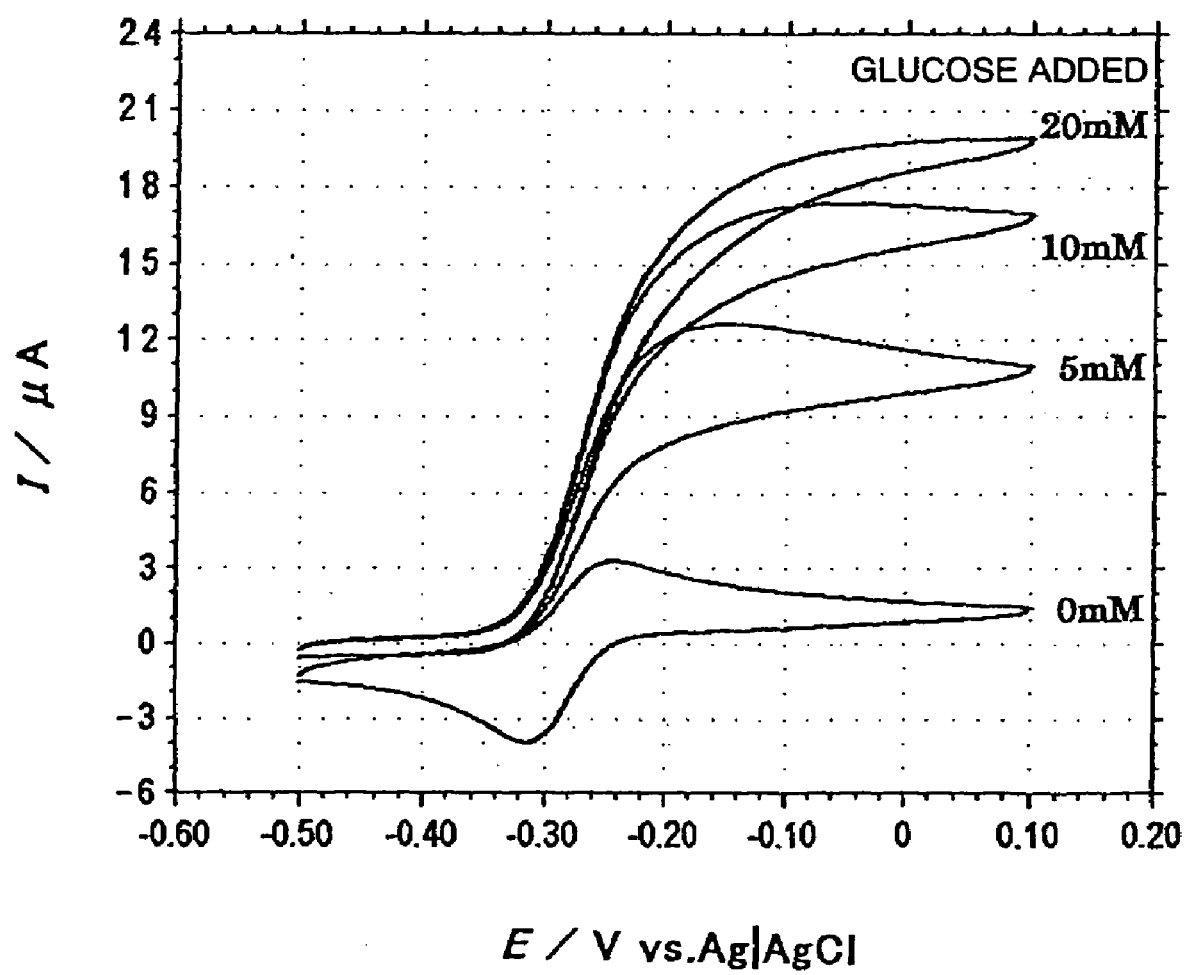
FIG. 7 is a schematic diagram showing a cyclic voltamogram obtained in Example 4.

In enzyme-immobilized electrodes according to Example 1, diaphorase as the enzyme and ACNQ as the electron acceptor compound were immobilized simultaneously. In Example 4, however, glucose dehydrogenase as another enzyme and NADH(NAD$^+$) as its coenzyme are additionally immobilized simultaneously. It has been confirmed that immobilization of glucose dehydrogenase enables extraction of a current from glucose (grape sugar). In this case, electrons propagate in the order of glucose→glucose dehydrogenase→NADH (NAD$^+$)→diaphorase→electron acceptor compound→electrode. The propagation of electrons after NADH has been explained in Example 1. Cyclic voltamogram obtained is shown in FIG. 7.

Next explained are applications of the enzyme-immobilized electrode according to the instant embodiment to electrode reaction-utilizing devices.

Figure 8:
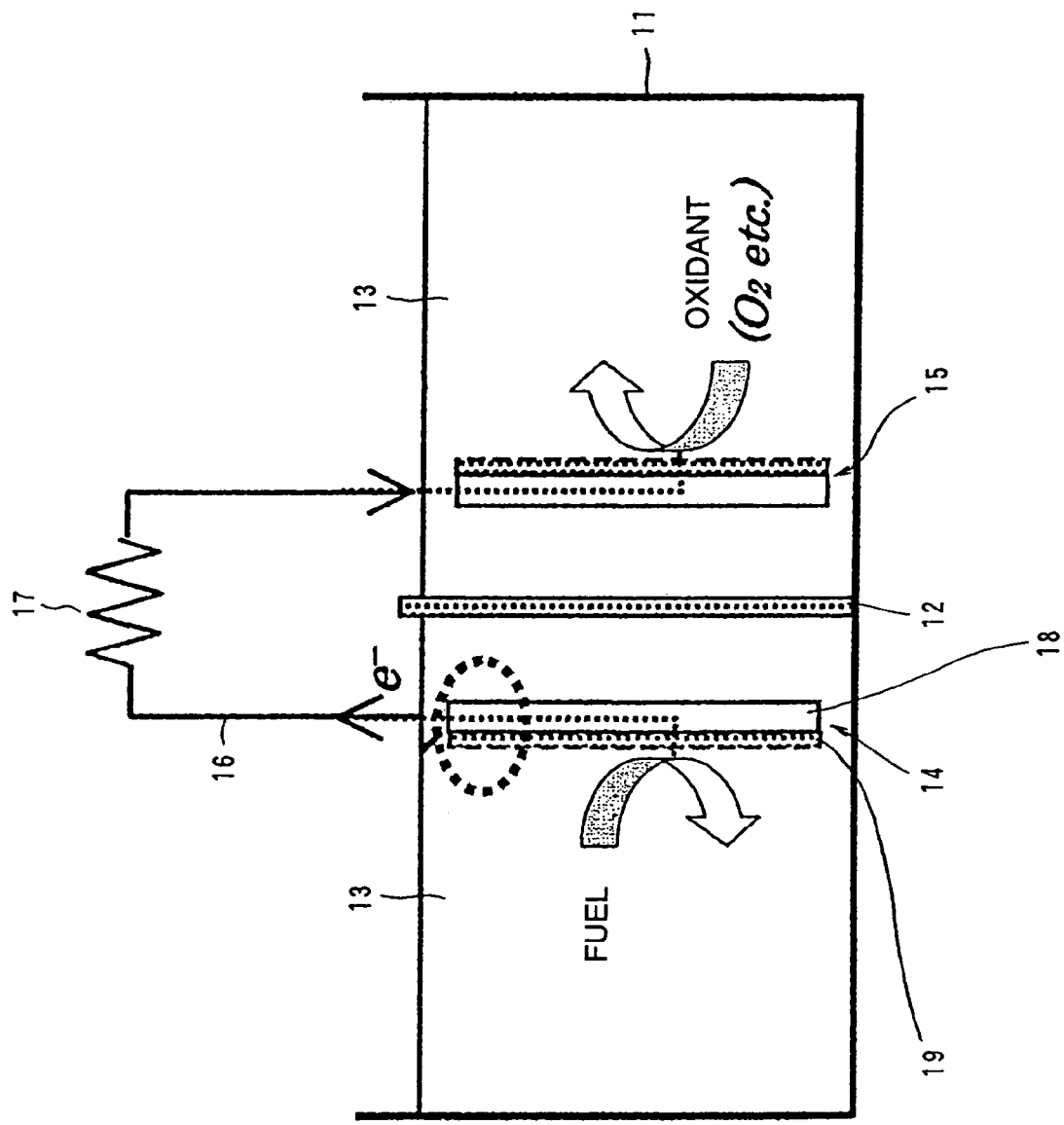
FIG. 8 is a schematic diagram showing a enzymatic fuel cell utilizing an enzyme-immobilized electrode according to an embodiment of the invention.

FIG. 8 shows an enzymatic fuel cell that is a bio fuel cell using the enzyme-immobilized electrode.

As shown in FIG. 8, the reaction vessel 11 in this enzymatic fuel cell is divided into two parts by a partition 12, and each part contains reaction solution 13. In one reaction solution 13 on one side of the partition 12, a bio cathode 14 (negative pole) is immersed. In the other reaction solution 13, a bio anode 15 (positive pole) is immersed. Between the bio cathode 14 and the bio anode 15, a load resistance 17 is connected via wiring 16.

Figure 9:
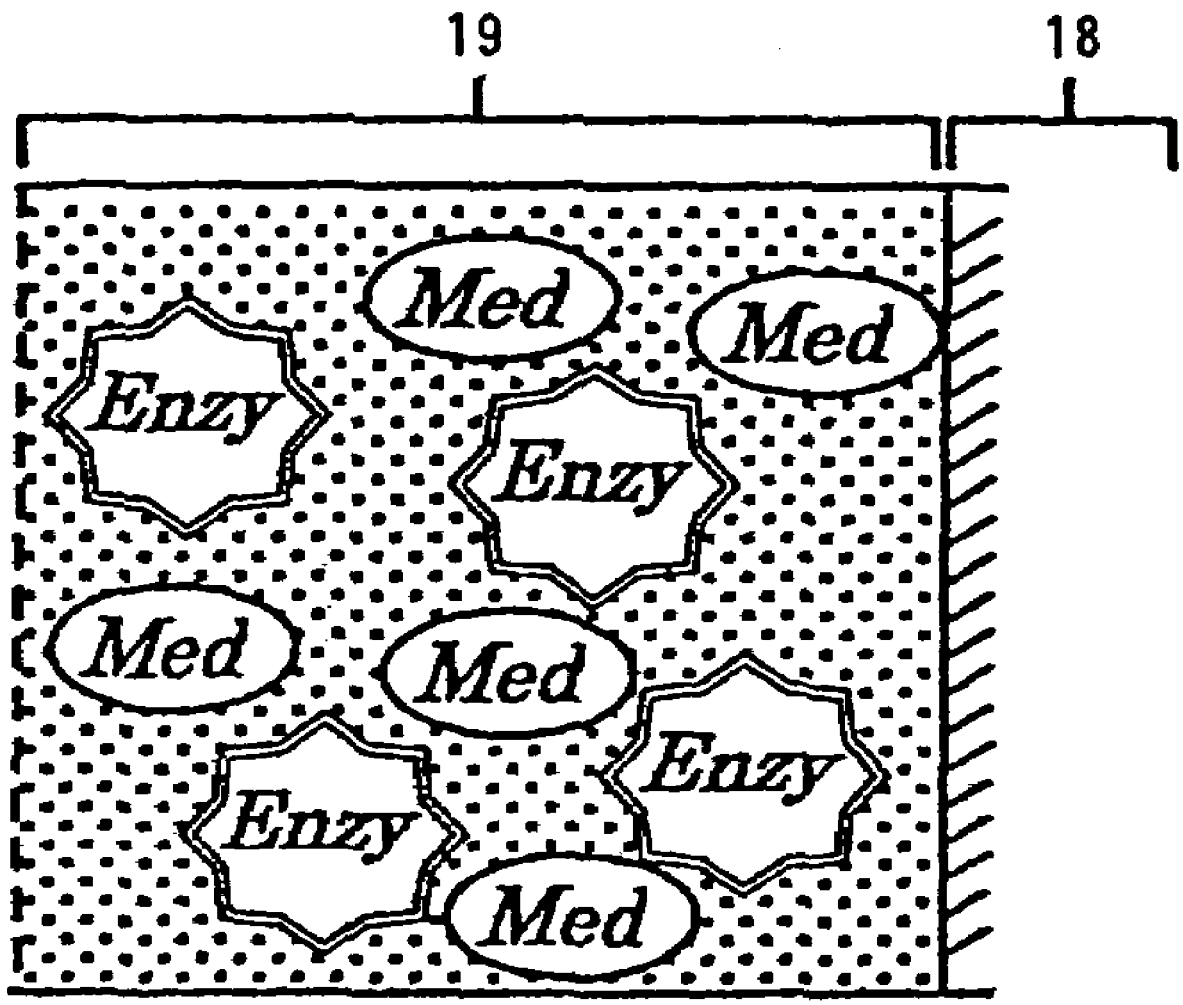
FIG. 9 is a schematic diagram showing a part of an enzyme-immobilized electrode used in the enzymatic fuel cell shown in FIG. 8 in an enlarged scale.

Enzyme-immobilized electrodes according to the embodiment are used as the bio cathode 14 and the bio anode 15, and each has a structure shown in FIG. 9, for example. As shown in FIG. 9, the bio cathode 14 and the bio anode 15 are made by forming an immobilized layer 19 of an enzyme and an electron acceptor compound layer on an electrode substrate 18. In FIG. 9, Enzy represents the enzyme, and Med represents the electron acceptor compound.

This enzymatic fuel battery generates electricity by feeding the bio cathode 14 with NADH as a fuel and feeding the bio anode 15 with oxygen or the like as an oxidant. In this case, in the bio cathode 14, electrons (e$^-$) supplied from NADH under the principle explained in conjunction with Example 1 are delivered to the electrode substrate 18 by the enzyme and the electron acceptor compound in the enzyme/ electron acceptor compound layer 19, and these electrons move to the bio anode 15 via the wiring 16 electricity, thereby generating electricity.

Figure 10:
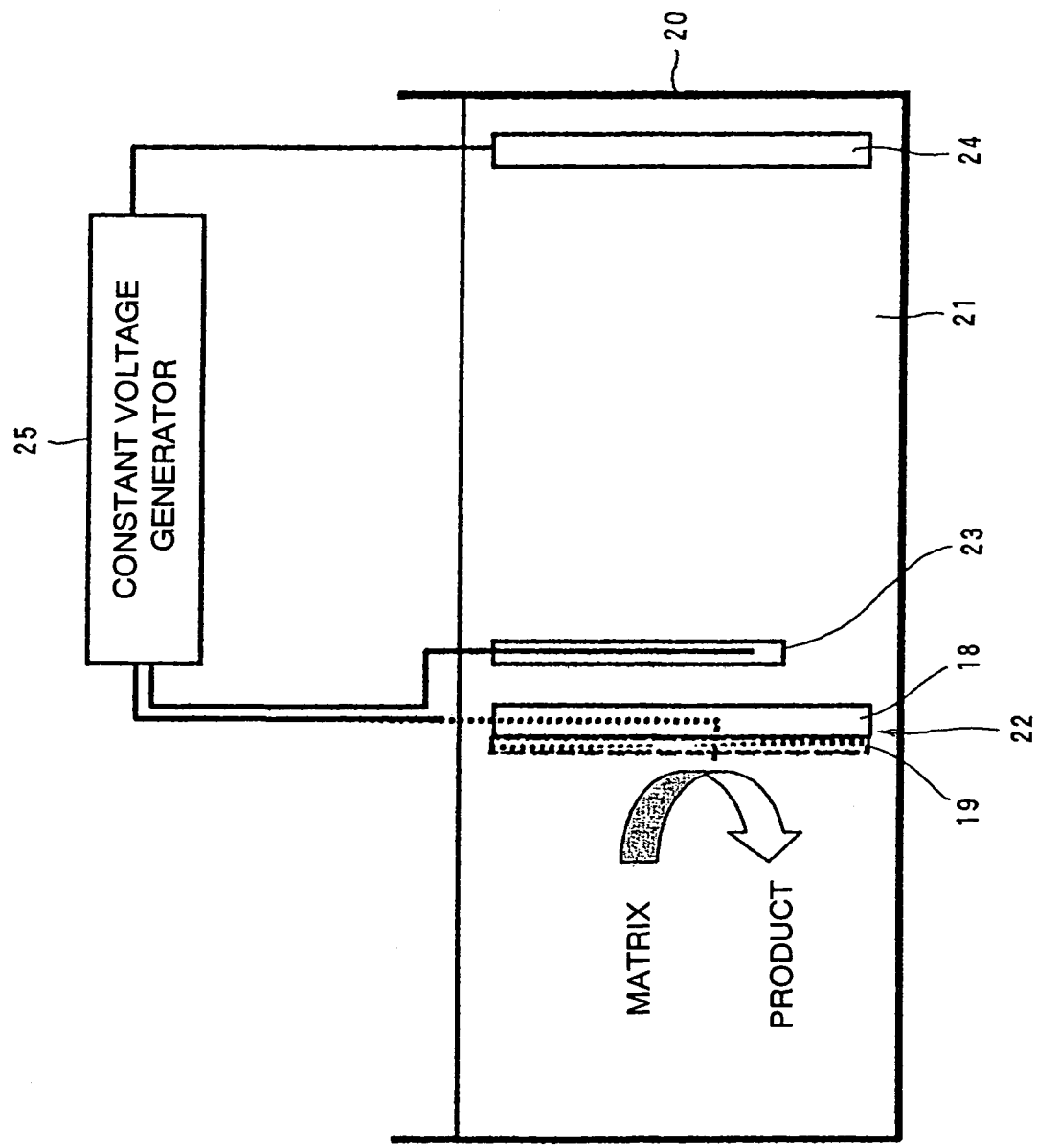
FIG. 10 is a schematic diagram showing a bioreactor using an enzyme-immobilized electrode according to an embodiment of the invention.

FIG. 10 shows a bioreactor using the enzyme-immobilized electrode.

As shown in FIG. 10, reaction solution 21 is contained in a reaction vessel 20 of the bioreactor, and a working electrode 22, reference electrode 23 and counter electrode 24 are immersed therein. An enzyme-immobilized electrode according to the embodiment is used as the working electrode 22, and it has a structure shown in FIG. 9, for example. A constant voltage generator 25 is connected between the reference voltage 23 and the counter electrode 24 such that the reference voltage 23 is held at a constant potential. The working electrode 22 is connected to a terminal to which the reference electrode of the constant voltage generator 25 is connected.

This bioreactor feeds the working electrode 25 with the matrix (for example, NADH) and brings about enzymatic reaction to generate a desired product.

As explained above, according to the embodiment, since an enzyme and an electron acceptor compound are immobilized simultaneously on an electrode to form an enzyme-immobilized electrode by using an immobilization carrier containing the electron acceptor compound in addition to glutaraldehyde and poly-L-lysine, it is possible to obtain a highly efficient functional electrode increased in immobilized amount of enzyme, capable of preventing elution of the enzyme almost completely, less susceptible to the balance of ambient electric charge, less variable in immobilized amount of enzyme and stability depending upon the service conditions, capable of maintaining the activity of the enzyme, and not subject to rate controlling of the entire reaction by the enzyme-immobilized electrode. In addition, the use of by using the enzyme-immobilized electrode leads to realization of high-performance electrode reaction-utilizing devices such as bio fuel cells, bioreactors, biosensors, or the like.

Heretofore, an embodiment and examples have been explained specifically. However, the invention is not limited to the embodiment and examples, but contemplates various changes and modifications based on the technical concept of the invention.

For example, numerical values, structures, materials, processes, and so on, are not but mere examples, and any other appropriate numerical values, structures, materials, processes, and so on, may be employed, if necessary.

According to the invention, it is now possible to immobilize an enzyme or simultaneously immobilize an enzyme and an electron acceptor compound to an electrode by an immobilization carrier in high density as well as to realize a highly efficient functional electrode capable of supply rate controlling of the matrix. Without rate controlling of performance of the electrode as the measuring system, it is now possible to review reaction systems in biosensors, bioreactors, bio fuel cells, and so on, in detail, which will greatly contribute to development of individual bio devices. Moreover, the invention is applicable to immobilization of an enzyme to elements or devices other than electrodes.

The invention claimed is:

1. An electrode comprising:
   an immobilization carrier which contains a first compound having at least two groups capable of polymerizing with amino groups or amino groups, and a second compound containing amino groups or amino groups;
   an electron acceptor compound wherein the electron acceptor compound is 2-amino-3-carboxy-1,4-naphthoquinone (ACNQ), being bonded to at least one of the first compound and second compound of the immobilization carrier; and an enzyme; wherein the enzyme is diaphorase.

2. An electrode according to claim 1, wherein the immobilization carrier has a structure in which the first compound and second compound are coupled by cross-linking.

* * * * *